United States Patent [19]

Bianco

[11] 4,119,450

[45] Oct. 10, 1978

[54] METHOD FOR MAKING A SANITARY PRODUCT

[76] Inventor: Carlo Bianco, Via Mezzanotte 104, Pescara, Italy

[21] Appl. No.: 672,810

[22] Filed: Apr. 1, 1976

[30] Foreign Application Priority Data

Apr. 4, 1975 [IT] Italy ............... 21990 A/75

[51] Int. Cl.² .................... B29C 17/04; B32B 1/10
[52] U.S. Cl. .................... 156/199; 156/276; 156/285; 264/89; 264/92; 264/93
[58] Field of Search .......... 264/89, 90, 92, 93, 264/248; 128/284, 286, 287, 288, 290 R, 290 H; 19/144.5; 425/388; 156/285, 199, 276; 28/121

[56] References Cited

U.S. PATENT DOCUMENTS

| | | | |
|---|---|---|---|
| 2,493,439 | 1/1950 | Braund | 264/92 |
| 2,896,387 | 7/1959 | Brock | 425/388 X |
| 3,471,600 | 10/1969 | Meek | 264/92 |
| 3,527,221 | 9/1970 | Croon et al. | 128/287 |
| 3,577,700 | 5/1971 | Bippus et al. | 425/388 X |
| 3,755,042 | 8/1973 | Robertson et al. | 264/90 X |
| 3,881,488 | 5/1975 | Delanty et al. | 128/287 |

FOREIGN PATENT DOCUMENTS 243,252   5/1960   Australia ................... 264/92

Primary Examiner—Jan H. Silbaugh
Attorney, Agent, or Firm—McGlew and Tuttle

[57] ABSTRACT

A method and arrangement for making a sanitary product. A pocket is formed in a waterproof web of synthetic plastic material by plastically deforming a portion of the web by application of heat and/or pressure. The web is further provided with retaining straps for securing the sanitary product on the body of a user. The invention constitutes a diaper holder or panty in one embodiment and permits a user to refill the pocket with absorbent napkin as desired. In another embodiment, the absorbent napkin is permanently sealed in the pocket by juxtaposing and securing another web of water-permeable material onto the waterproof web.

5 Claims, 7 Drawing Figures

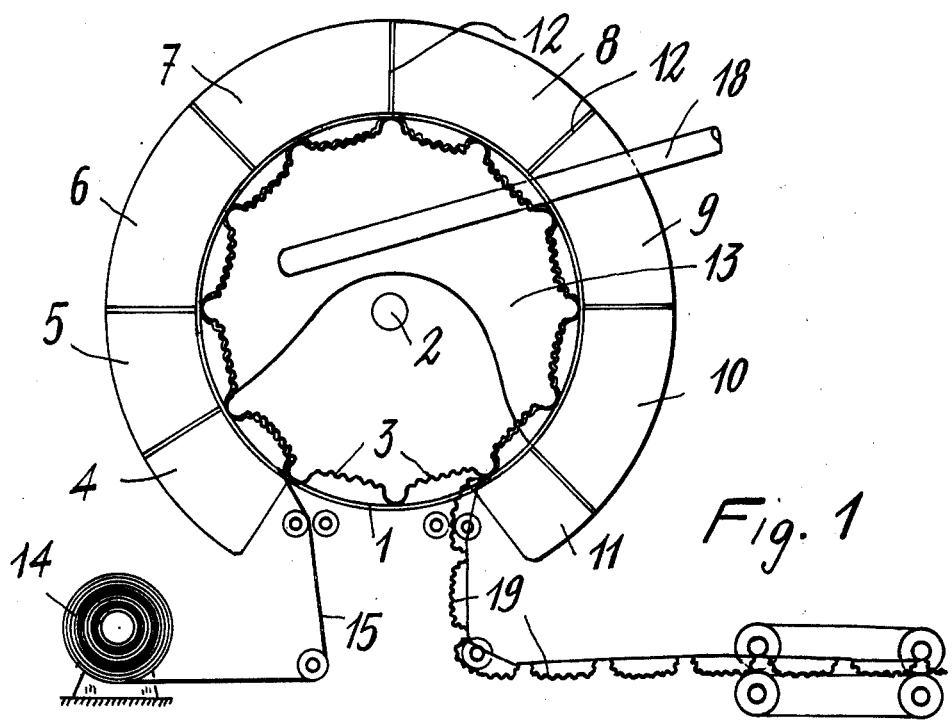
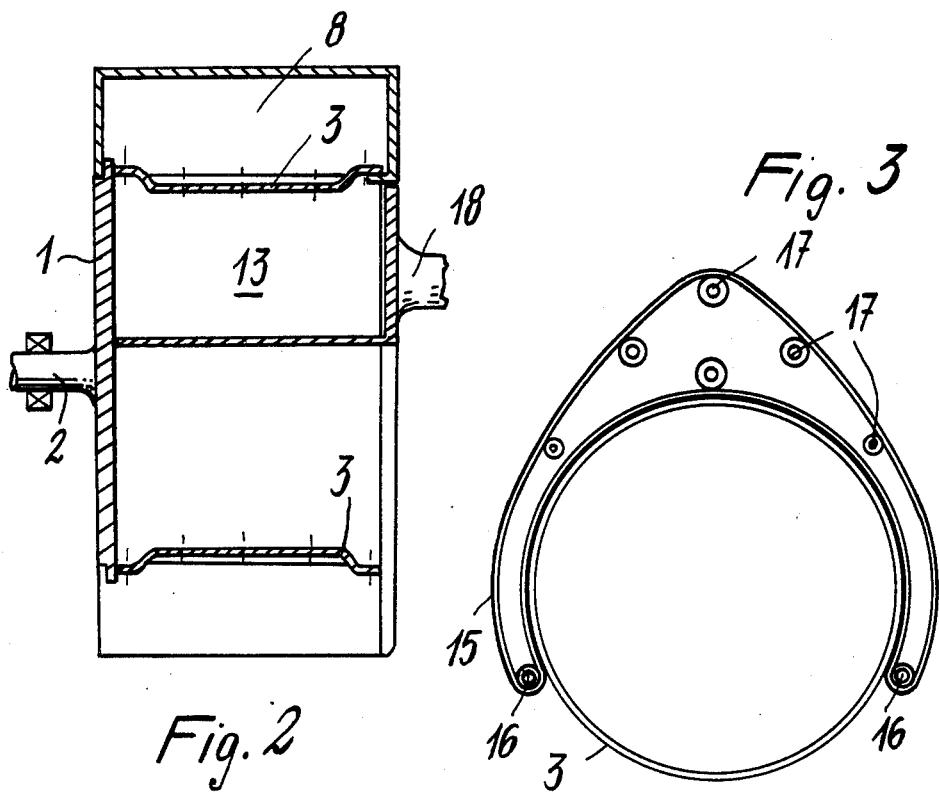

METHOD FOR MAKING A SANITARY PRODUCT

BACKGROUND OF THE INVENTION

This invention relates to a process of making napkins-bearing knickers or diaper holders and napkins-knickers or diapers provided with a pocket or the like as established by deforming a plastic material web comprising the product, so that the napkin or in any case the absorbing layer may be located within said pocket an arrangement and method for making the sanitary product is also disclosed.

Many types are commercially known of napkins-knickers and also napkins-bearing knickers (the former term is intended to designate a diaper, i.e. a napkin associated with a plastic container which is adapted to be secured to a baby's body; the latter term is intended to designate a diaper holder or panty comprising a simple plastic support which is adapted to be repeatedly filled with interchangeable conventional napkins) that generally suffer from the drawback of not ensuring good liquid sealing at a baby's legs and not sufficiently "dressing" the baby's body. This is essentially due to the fact that, the starting plastic sheet (used as a covering or support) is flat and therefore is unsuited to the tridimensional conformation about a baby's body because of the interposition of the inner napkin thickness, and this causes many disadvantages.

Summary of the Invention

In order to overcome such disadvantages, the present invention proposes:

(1) Napkins-knickers and napkins-bearing knickers provided with a pocket or the like as established by deformation of the particular configuration of a plastic material web comprising the sanitary product;

(2) a process of making sanitary products of the above mentioned type, fitted with a central pocket provided by deforming and stretching the starting flat plastic sheet; and (3) a machine for carrying out said process.

The process according to the invention substantially provides a continuous processing for the plastic material sheet which is caused to follow a confined path at preferably gradually increasing temperatures and pressures, and progressively deforming the sheet until it conforms to the configuration of corresponding dies or modls, the surface of which is preferably undulated or highly corrugated.

A machine arrangement for carrying out the process according to the invention substantially provides a continuously rotating drum having a surface provided with a plurality of dies or molds (with preferably undulated or corrugated surfaces). The processing material bears against the outer surface of the drum being affected by one or more chambers of preferably increasing temperatures and pressures. One or more highly evacuated chambers are internally provided within the drum and suitable holes are provided on said surface.

A machine according to the invention may be completed on an assembly line, wherein at one work station a suitably shaped small mattress or napkin is laid in the built up pockets, and at a successive station a layer of suitable material, such as particularly non-woven fabric, is juxtaposed over the napkin thus covering the product, and is sealed thereto. Finally, a station is provided for applying and then sealing to the sanitary product such binding members as strings, preferably T-fashion arranged at the ends. Of course, the machine as a whole is suitable for making napkins-knickers. If only the pocket forming and string sealing stations were used, the machine can be used for making napkins-bearing knickers.

BRIEF DESCRIPTION OF THE DRAWINGS

The present invention can be more clearly understood from the following detailed description, given by mere way of unrestrictive example, particularly referring to the figures of the accompanying drawings in which:

FIGS. 1 and 2 are side and sectional views, respectively, showing the machine station for providing pockets in a continuous operation from the flat sheet;

FIG. 3 is a schematic side view showing a belt device for steadily holding the flat side zones of the plastic web;

Description of the Preferred Embodiments

Figure 4:
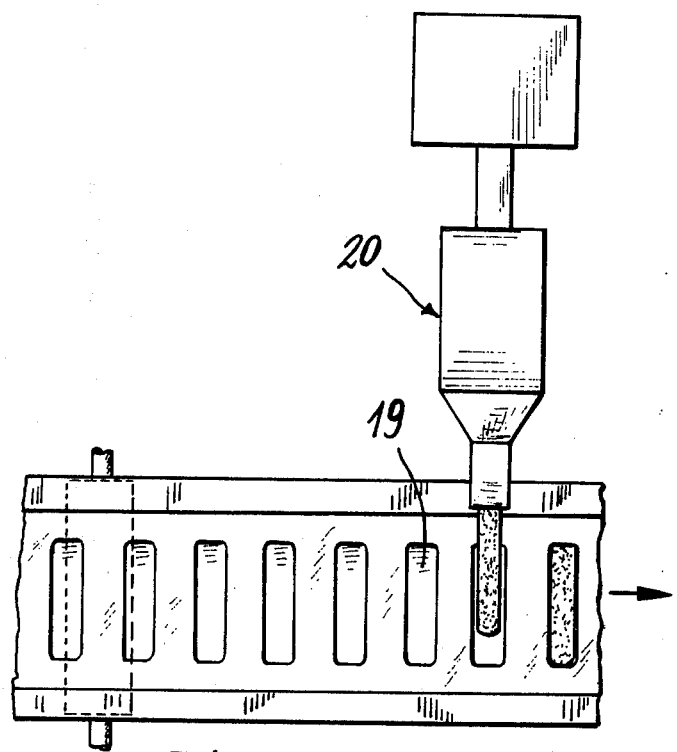
FIG. 4 is a schematic top view showing a station, wherein preformed small mattresses are positioned inside the previously formed pockets.

The machine station particularly shown in FIGS. 1–3 substantially comprises a large drum or support 1 mounted for rotation on a shaft 2. The outer surface of the drum is formed with a series of concave dies or molds 3, the contour of each of such depressions substantially corresponding to that of the desired pocket. The spacing between one and another die or mold is designed to provide for the required gap in cutting two flat side bands of two adjoining sanitary products.

Particularly, in accordance with an essential feature of the invention, said concave dies or molds 3 have undulated or corrugated surfaces.

Externally of drum 1 and for the majority of the outer surface, there are provided a series of adjoining toresector chambers 4–11, separated from one another by partitions or walls 12 preferably having gate members thereon. Internally of the rotating drum a stationary chamber 13 is provided, also involving most of the inner surface of the drum and, in the case shown in FIG. 1, involving the whole inner surface relating to chambers 5–10. This station is completed by feeding means such as a reel 14 for continuously supplying a synthetic plastic material sheet or web 15 which, as suitably driven by conventional rollers, entirely covers the inner surface of the drum. In order to maintain the external edges or borders of said flat sheet 15 completely adhering to the flat side edges of drum 3, two devices can be used on opposite sides of the drum. Such devices may employ a belt 15' synchronously rotating with drum 1, and suitably driven by rollers 16 maintaining the borders of the sheet adherent to drum 1 throughout the processing zone, and further rollers 17 for simple guide and transmission purposes.

It should be noted that the above described devices for retaining the flat edges or borders of a sheet being processed can be arranged both internally and externally of the drum.

According to the invention, within chambers 4–11 preferably increasing temperatures and pressures are provided which, by mere way of example may be: 60° C and 5/100 ATE for chamber 5; 65° C and 7/100 ATE for chamber 6 and the same increments for chambers 7, 8 and 9 until a temperature of about 100° C and a pressure of 15/100 ATE is obtained in chamber 10. On the other hand, by aspiration through tube 18 a high vacuum is built up in chamber 13 which vacuum may be, for example, on the order of −0.5/0.6.

The operation of this first station will be apparent from the foregoing and may be briefly summarized as follows. Flat plastic material sheet 15 enters the station and completely wraps around drum 1 with its side edges or borders firmly retained against the drum by the top pressure, bottom vacuum and action of said belts 15. Centrally of the web at the molding dies 3 the gradual action of temperature and pressure (pressure outside and vacuum inside) cause the plastic material to be gradually formed by stretching, until this material perfectly matches the shape of the corrugated surface molds at end chambers 9 and 10. Small diagrammatically-illustrated holes or orifices are provided on the edge and/or bottom of said molds or dies. Therefore, at the outlet of this station, a sheet of plastic material will be provided having at its central zone a series of impressions or pockets, preferably with a corrugated surface designated by 19 in FIGS. 5a and 5b.

It should be noted that according to the invention, also considering the materials being used, said external chambers 4–11 could comprise a single chamber or be dispensed with as pressure chambers, thereby assigning the task of providing for deformation only to the vacuum provided within internal chamber 13. In lieu of said pressure chambers, other means could be provided, such as, for example, simple heating means. Furthermore, according to the invention, supply or feeding film 15 could be preheated by hot rollers or could be passed through preheating chambers prior to introduction into the drum.

Finally, it should be noted that the flat outer edges or borders of the web can be maintained adhering to the drum surface on the pocket sides by a series of small holes or orifices communicating with inner chamber 13, wherein said vacuum has been built up. Just this vacuum is responsible for perfect adhesion of the flat sides against the drum, while deformation of plastic material occurs at said pockets. To this end, it should be noted that by means of some technical expedient, such as for example simple scorings on the drum surface between said small holes or orifices and mold concavity, the plastic material could be deformed even without providing holes or orifices on the bottom of the dies or molds communicating with said vacuum chamber 13.

According to the invention, the web of plastic material thus treated and provided with a series of preferably corrugated pockets is supplied to a next station (see FIG. 4) where, in connection with the continuously running web, a station designated as a whole at 20 is provided. This station 20 feeds small mattresses of absorbent material that are to be positioned in each of said pockets 19. Such mattresses may be of any type, having one or more plies, folded or not folded up by a single lap. Said station 20 is not herein described in detail, since it can be of any known type with a single plied lap or laps folded up according to G, S or Z shape to provide a three-ply small mattress, of which preferably at least one ply can be entirely or partially of pressed type.

According to the invention, a further station is provided (see FIG. 5), wherein the sheet of plastic material, provided with pockets 19 containing small mattresses 21 supplied from station 20, is covered with a layer 22 of soft permeable material, such as non woven fabric, from a reel 23, and covers the entire surface of the plastic material. Sealer rollers 24 provide for sealing this layer or ply to that of the plastic material at the longitudinal edges, whereas transverse or cross sealing is effected by two or more sealer rollers or cylinders 25. Subsequent cutting rollers or cylinders 26 provide for final cutting.

Figure 5A:
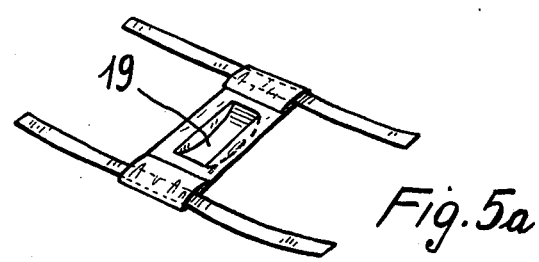
FIGS. 5a and 5b respectively show a piece of napkins-bearing knickers and napkin-knickers as obtained in accordance with the invention.
Figure 5:
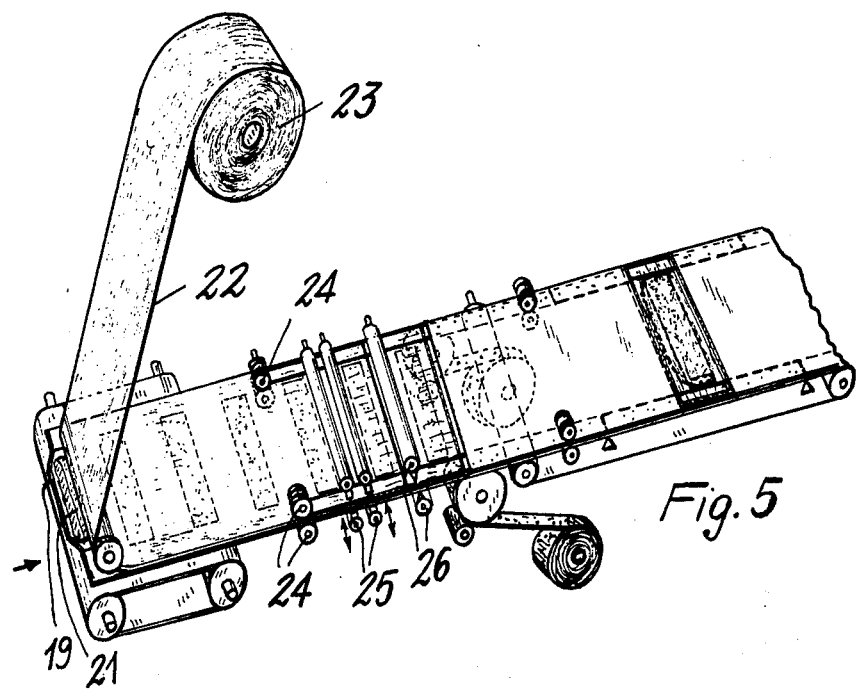
FIG. 5 schematically shows a station for finishing the sanitary products with possible covering layer and strings.

Cavities 3 include side walls 3b and transverse corrugations 3c and drum 1 includes a surface 3a around and adjacent the cavities 3. As best seen in FIG. 4, after pockets 19 are formed in waterproof web 15 they include side walls 19a corresponding with the side walls 3b of the cavity 3, and transverse corrugations. A web surface 15a remains around the cavities 19 and the water absorbent material is deposited in the cavities 19 to be held against transverse and longitudinal movement by the side walls 19a. As best seen in FIG. 5, water absorbent web 22 is fed over the waterproof web 19 flush with the web surface 15a, and the two webs are sealed to each other along portions of the web surface 15a by rollers 24 and 25.

At this station, or at a next subsequent station, cross or transverse strips can be finally arranged and sealed at the minor sides of the sanitary product, such strips acting as strings in use. These strings can be also made of plastic material or non woven fabric or material.

Figure 5B:
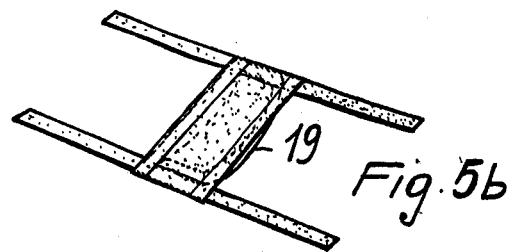

As stated in the foregoing, the machine according to the invention enables as a whole to obtain napkins-knickers. If only the station shown in FIGS. 1–3 and the final station shown in FIG. 5 for string sealing were used, napkins-bearing knickers are obtained. By mere way of indication, FIGS. 5a and 5b illustrate, respectively, a piece of napkin-bearing knickers and napkin-knickers according to the invention, as obtained by the process and machine above described.

What is claimed is:

1. A method of making a sanitary product, particularly a diaper, comprising; providing a web of waterproof material, feeding said waterproof web to a surface with an indented shaping cavity having transverse corrugations and side walls, deforming a portion of said waterproof web by heating and applying pressure until said waterproof web portion conforms to the contour of said cavity and a pocket is formed in said web having transverse corrugations and sidewalls leaving a web surface around said pocket, advancing said waterproof web portion and web surface sequentially through a plurality of zones in each of which the temperature and pressure are progressively higher than in the preceding zones, inserting absorbent material into said pocket so that it is held against lateral and transverse movement by said side walls, feeding a water-permeable covering web which is substantially coextensive with said waterproof web over said absorbent material and flush with said web surface, and sealing both of said webs to each other along at least a portion of said web surface.

2. A method as defined in claim 1, wherein said step of deforming further comprises applying positive pressure to the outer surface of said web portion which faces away from said cavity.

3. A method as defined in claim 1, wherein said step of deforming further comprises applying a vacuum to the inwardly-directed surface of said web portion which faces towards said cavity.

4. A method as defined in claim 1, wherein said step of heating is performed by heating said synthetic plastic material web portion from room temperature to a final temperature in which the synthetic plastic material begins to soften and flow.

5. A method as defined in claim 1; and further comprising the step of preheating said web prior to feeding said web portion into said cavity.

* * * * *